United States Patent [19]

Christensen

[11] Patent Number: Plant 5,702

[45] Date of Patent: Apr. 1, 1986

[54] HYBRID MINIATURE ROSE PLANT CV. AROGOBI

[75] Inventor: Jack E. Christensen, Ontario, Calif.

[73] Assignee: Armstrong Nurseries, Inc., Ontario, Calif.

[21] Appl. No.: 639,748

[22] Filed: Aug. 13, 1984

[51] Int. Cl.[4] ..... A01H 5/00

[52] U.S. Cl. ..... Plt./7

[58] Field of Search ..... Plt./7

*Primary Examiner*—Robert E. Bagwill

*Attorney, Agent, or Firm*—Synnestvedt & Lechner

[57] ABSTRACT

An upright to spreading rose plant of the hybrid miniature class, having a more-than-average resistance to mildew and rust, and producing an abundance of large, well-formed buds and flowers of a bicolor orange coloration, the darker color being carried on the outside surface of the petals, rather than on the inside surface as is usual among bicolor roses. Bloom production is nearly continuous throughout the growing season. The plant bears attractive, semi-glossy foliage which is relatively large for the class and bears very few prickles on its canes and stems.

1 Drawing Figure

This invention relates to a new variety of hybrid miniature rose cv. Arogobi. The plant is an outdoor seedling of the miniature bush type, cultivated primarily for garden decoration; its hardiness is as yet untested. It was first propagated by Jack E. Christensen in Ontario, Calif., having as its seed parent Cricket (U.S. Plant Pat. No. 4,663) and as its pollen parent Golden Wave (U.S. Plant Pat. No. 2,105).

The new rose cv. Arogobi is particularly distinguishable from other presently commercialized rose cultivars by the following combination of characteristics: its unique bicolor orange flower coloration, essentially as described and illustrated herein, in which the darker of the two colors in the flower is carried on the outside surface of the petals, unlike most bicolor roses, in which the darker color is carried on the inside surface of the petals; its large, well-formed buds and blooms carried on a low-growing bush; its very low incidence of prickles on the canes and stems; and its attractive, semi-glossy foliage, which is relatively large for the class. The new variety preserves its distinguishing characteristics through succeeding propagations by cuttings and budding.

This new cultivar may be distinguished from its seed parent, Cricket (U.S. Plant Pat. No. 4,663), by the following combination of characteristics: Cricket produces flowers of a relatively uniform orange coloration, whereas the new seedling produces flowers of a bicolor orange coloration, essentially as described and illustrated herein. Whereas the new rose produces flowers of a 1½- to 2-inch diameter, Cricket produces significantly smaller flowers of a 1- to 1½-inch diameter. The new rose is a moderately vigorous, medium-height bush for the class, whereas Cricket is a very vigorous, significantly taller bush for the class. Cricket produces very heavy canes for the class, whereas the new seedling produces significantly lighter canes.

The new cultivar may be distinguished from its pollen parent, Golden Wave (U.S. Plant Pat. No. 2,105), by the following combination of characteristics: Golden Wave produces flowers of a relatively uniform yellow coloration, whereas the new rose bears flowers of a bicolor orange coloration, essentially as described and illustrated herein. Whereas the new cultivar is classified as a hybrid miniature, Golden Wave is classified as a hybrid tea. Golden Wave produces flowers of 22 to 30 petals, whereas the new rose produces flowers with significantly fewer petals (18 to 23). Whereas the flowers of Golden Wave are very fragrant, the flowers of the new rose are only slightly fragrant. The flowers of Golden Wave are more than twice as large in diameter as the flowers of Arogobi.

The accompanying drawing illustrates the new variety in color as grown in Ontario, Calif., and shows the flowering thereof from bud to full bloom.

Throughout this specification, color names beginning with a small letter signify that the name of that color as used in common speech is aptly descriptive. Color names beginning with a capital leter designate values based on The R.H.S. Colour Chart published by The Royal Horticultural Society of London, England.

The descriptive matter which follows pertains to roses grown in Ontario, Calif. and is believed to apply to similar conditions of soil and climate elsewhere.

FLOWER

The new variety bears its flowers sometimes singly, sometimes three to four or more to a stem, in regular, rounded clusters on stems of normal strength and medium length for miniature roses. Outdoors, the plant blooms abundantly and nearly continuously throughout the growing season. The blooms have a slight tea fragrance.

BUD

The peduncle is long for the class, of average to heavy caliper, strong and stiff. It is moderately smooth, with numerous stipitate glands and numerous small hairs on its surface. The color of the peduncle is between Yellow-Green 144A and Green 137B.

Before the calyx breaks, the bud is medium to large in size for miniature roses, and long, pointed and ovoid in form. There is a conspicuous neck to the bud, and there are few foliaceous appendages and few stipitate glands on the bud surface. There are usually slender foliaceous parts present which extend beyond the tip of the bud, equal to one half or more of its length.

As the calyx breaks, the color of the bud is between Orange-Red 34B and Orange-Red 34C. The inner surface of the sepals carries a fine, woolly tomentum; margins are lined with stipitate glands and hairs.

As the first petal opens, the bud is average to large in size for the class and long, pointed and ovoid in form. On the outside of the petals is a basal attachment zone near Yellow 7A in color, with the remainder of the petal surface quickly diffusing to between Orange-Red 34C and Orange-Red 34B. On their inside surface, the petals display a basal attachment zone near Yellow 7A which quickly suffuses to between Orange 24A and Orange 26B. The bud opens up well and is not prevented from opening by cold, hot, wet or dry weather.

BLOOM

The size of the bloom when fully open is large for miniature roses, being from 1½ to 2 inches (4 to 5 centimeters) in diameter. Petalage is double, with petals arranged regularly. Petals number from 18 to 23, and there may be from 1 to 4 petaloids present.

Bloom form when half open is moderately high-centered, with petals somewhat cupped and petal edges somewhat reflexed outward. When fully open, the bloom is semi-flat to cupped, with petals similarly flat and loosely cupped and with petal edges very reflexed to quilled outward.

The petals are thick in texture and of moderately heavy to crisp substance, with insides slightly shiny to satiny and outsides slightly satiny. The outside petals are nearly round to broadly obovate, with apices sometimes rounded but usually bearing one small point. The intermediate petals are broadly obovate, with apices sometimes rounded but usually bearing one small point. Inside petals are narrowly obovate, with apices like those of the outside and intermediate petals. Petal colors may be modified by being shaded or washed or tinted with other colors.

The paragraph immediately following describes the color values observed in a newly opened flower from a plant grown in a greenhouse in Ontario, Calif. in the month of August.

The outside surface of all petals—outside, intermediate and inside—is essentially the same in coloration, having a basal attachment zone near Yellow 7A which quickly suffuses in the remainder of the petal surface to between Orange-Red 34C and Orange-Red 34B. The inside surface of the outside, intermediate and inside petals displays a basal attachment zone near Yellow 7A which suffuses to between Orange 24A and Orange 26B.

The following paragraph describes the color values observed in a flower which had been open for three days in the month of August. The plant was grown in a greenhouse in Ontario, Calif.

The outside surface of the outside and inside petals has a basal attachment zone near Yellow 6C, which quickly suffuses to between Orange-Red 34D and Orange-Red 35C in the remainder of the petal surface. The inside surface of the outside and inside petals displays a basal attachment zone near Yellow 6C, with the remainder of the petal surface suffusing to between Orange 29D and Yellow-Orange 23D.

The general color effect of the newly opened flower is between Orange 24A and Orange 26B. The general color effect of the flower three days after opening is between Yellow-Orange 23D and Orange 29D. The petals usually drop off cleanly and are not particularly affected in this respect by cold, hot, wet or dry weather.

The flower on the bush in the garden persists for 3 to 4 days in the month of August. Roses cut from plants grown outdoors in August persist for 4 to 5 days at living-room temperatures.

REPRODUCTIVE ORGANS

The stamens are numerous and are arranged regularly about the pistils. Filaments are medium to long in length; most bear anthers which are medium to large in size. Anthers all open approximately at once. Anther color is near Yellow-Orange 17C when immature and near Greyed-Orange 165A at maturity. Pollen is abundant and near Yellow-Orange 17D in color.

The pistils are average to many in number (approximately 40). The styles are uneven, short to average in length, of thin to average caliper, and somewhat loosely bunched. The stigma is near Yellow 2C in color. Ovaries are all enclosed in the calyx.

Hips are globular in shape and of average length; they are moderately smooth with thick, fleshy walls. Hip color is near Yellow-Green 154C.

Sepals fall soon.

Seeds are average in number (approximately 12 to 20) and are medium in size.

FOLIAGE

The compound leaves usually comprise 3 to 5 leaflets. They are present in normal quantity and are medium to large in size for miniature roses. Leaves are moderately heavy and semiglossy. The leaflets are oval to ovate in shape, with acute apices and round bases. Margins are simply serrate.

The upper surface of the mature foliage is between Yellow-Green 147A and Green 139A in color; the under surface is near Greyed-Green 191A. The upper surface of the young foliage is between Yellow-Green 147A and Green 139A in color, washed heavily with near Greyed-Purple 187A. The under surface of the young foliage is near Greyed-Green 191A, washed heavily with near Greyed-Purple 183D.

The rachis is average in size and heavy, grooved on its upper side with few stipitate glands on the edges. The under side is sparsely prickly. Stipules are of medium length and are moderately narrow, with medium-length points, turning out at an angle of usually less than 45°.

The plant displays a more-than-average resistance to mildew and rust when compared to other cultivars now in commerce grown under comparable conditions in Ontario, Calif.

GROWTH

The plant is a miniature variety of medium height, bushy, moderately branched, and upright to spreading in habit. Its growth is moderately vigorous. Canes are of medium caliper for miniature roses.

The main stems are between Yellow-Green 146C and Green 139C in color. They bear very few large prickles which are medium-length to long for the class, almost straight, with moderately narrow bases of medium length. Large prickle color is near Greyed-Orange 166C. There are no small prickles and no hairs.

The branches are between Yellow-Green 146A and Green 139A in color. They bear a few large prickles which are medium to long in length for the class, almost straight, with moderately narrow bases of medium length. These prickles are near Greyed-Orange 174B in color. There are no small prickles and no hairs.

New shoots are between Yellow-Green 147A and Green 139A in color, washed with near Greyed-Purple 187A. They bear a few large prickles which are medium-length to long for the class, almost straight, with moderately narrow, medium-length bases. Prickle color is near Greyed-Red 178D. There are no small prickles and no hairs.

I claim:

1. A new and distinct variety of rose plant of the hybrid miniature class, substantially as herein shown and described, being especially characterized in the unique bicolor orange coloration of its flowers, essentially as described and illustrated herein, in which the darker of the two colors is carried on the outside surface of the petals, unlike most bicolor roses, in which the darker color is carried on the inside surface of the petals; its large, well-formed buds and blooms borne on a low-growing bush; its very low incidence of prickles on the canes and stems; and its attractive, semi-glossy foliage, which is relatively large for the class.

* * * * *

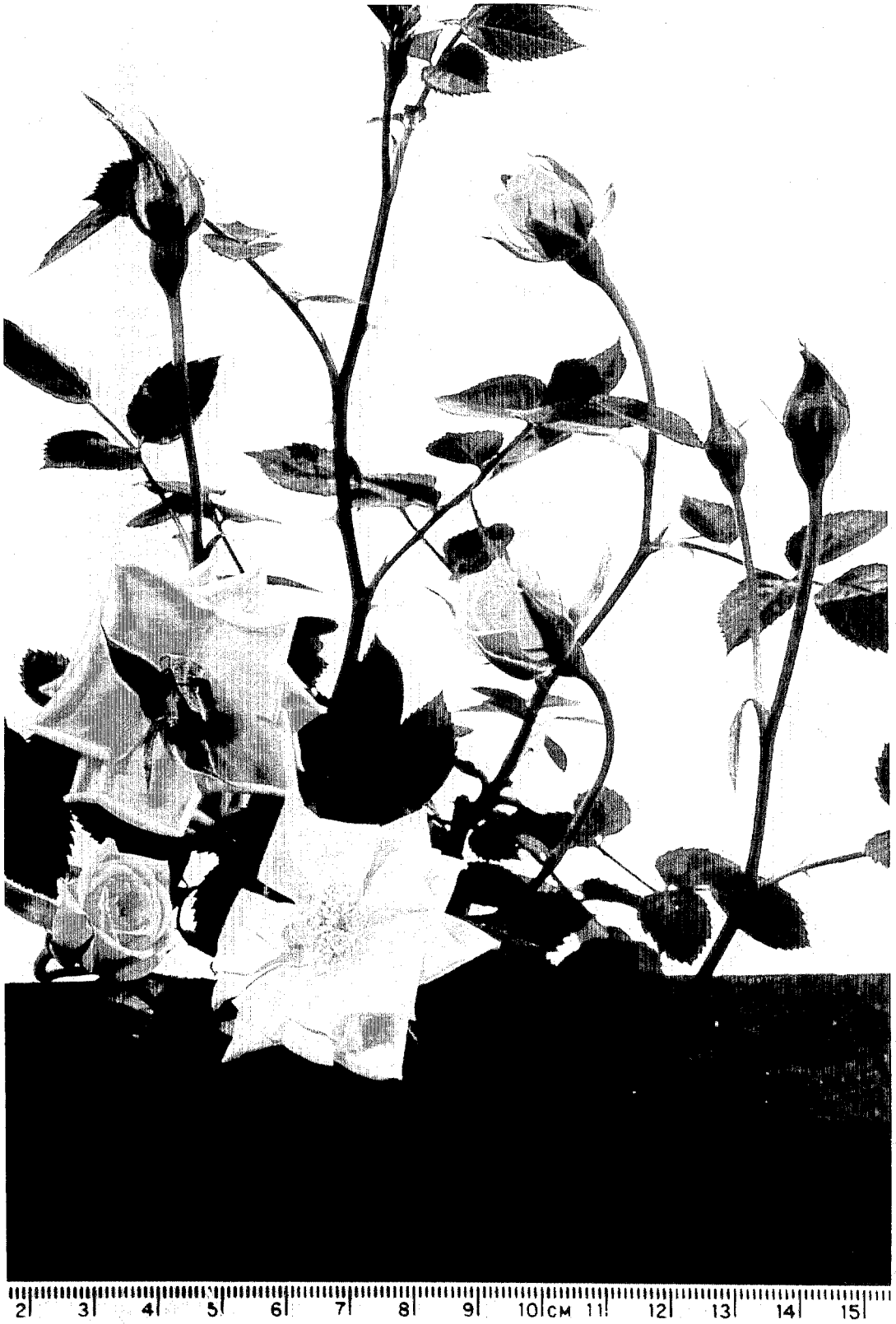
2 3 4 5 6 7 8 9 10 CM 11 12 13 14 15